(12) United States Patent
Bhattacharya et al.

(10) Patent No.: US 12,106,196 B2
(45) Date of Patent: Oct. 1, 2024

(54) METHOD AND SYSTEM FOR GENERATING SYNTHETIC TIME DOMAIN SIGNALS TO BUILD A CLASSIFIER

(71) Applicant: Tata Consultancy Services Limited, Mumbai (IN)

(72) Inventors: Sakyajit Bhattacharya, Kolkata (IN); Oishee Muzumder, Kolkata (IN); Aniruddha Sinha, Kolkata (IN); Dibyendu Roy, Kolkata (IN); Avik Ghose, Kolkata (IN)

(73) Assignee: Tata Consultancy Services Limited, Mumbai (IN)

( * ) Notice: Subject to any disclaimer, the term of this patent is extended or adjusted under 35 U.S.C. 154(b) by 853 days.

(21) Appl. No.: 17/196,406

(22) Filed: Mar. 9, 2021

(65) Prior Publication Data

US 2021/0342641 A1 Nov. 4, 2021

(30) Foreign Application Priority Data

Apr. 30, 2020 (IN) .............................. 202021018573

(51) Int. Cl.
*G06N 20/10* (2019.01)
*G06F 18/2134* (2023.01)
*G06F 18/214* (2023.01)
*G06F 18/2321* (2023.01)
*G06F 18/243* (2023.01)
(Continued)

(52) U.S. Cl.
CPC ......... *G06N 20/10* (2019.01); *G06F 18/2134* (2023.01); *G06F 18/2148* (2023.01); *G06F 18/2321* (2023.01); *G06F 18/24317* (2023.01); *G16H 50/20* (2018.01); *G16H 50/70* (2018.01); *G06F 2218/14* (2023.01)

(58) Field of Classification Search
CPC .................................................. G06F 16/7867
See application file for complete search history.

(56) References Cited

FOREIGN PATENT DOCUMENTS

KR 102002549 B1 7/2019

OTHER PUBLICATIONS

Vidhya V et al., "Synthetic ECG and PPG signal generation using pulse shaping technique," Annual IEEE India Conference (INDICON), Dec. 2015, IEEE, https://ieeexplore.ieee.org/document/7443256.
(Continued)

*Primary Examiner* — Pei Yong Weng
(74) *Attorney, Agent, or Firm* — Finnegan, Henderson, Farabow, Garrett & Dunner, LLP

(57) ABSTRACT

State of the art systems and methods attempting to generate synthetic biosignals such as PPG generate patient specific PPG signatures and do not correlate with pathophysiological changes. Embodiments herein provide a method and system for generating synthetic time domain signals to build a classifier. The synthetic signals are generated using statistical explosion. Initially, a parent dataset of actual sample data of class and non-class subjects is identified, and statistical features are extracted. Kernel density estimate (KDE) is used to vary the feature distribution and create multiple data template from a single parent signal. PPG signal is again reconstructed from the distribution pattern using non-parametric techniques. The generated synthetic data set is used to build the two stage cascaded classifier to classify CAD and Non CAD, wherein the classifier design enables reducing bias towards any class.

9 Claims, 9 Drawing Sheets

(51) Int. Cl.
G16H 50/20 (2018.01)
G16H 50/70 (2018.01)

(56) References Cited

OTHER PUBLICATIONS

Pavol Dolinský et al., "Model for Generating Simple Synthetic ECG Signals," Acta Electrotechnica et Informatica, Sep. 2018, vol. 18, No. 3, Research Gate, http://www.aei.tuke.sk/papers/2018/3/01_Dolinsky.pdf.
M. Marsousi et al., "A flexible approach for simulating physiological signals," Acta Electrotechnica et Informatica, May 2013, vol. 34, No. 3, Pub Med, https://www.ncbi.nlm.nih.gov/pubmed/23719193.
Durga Toshniwal et al., "Multistage Classification for Cardiovascular Disease Risk Prediction," Proceedings of the 4th International Conference on Big Data Analytics, 2015, vol. 9498, pp. 258-266, ACM https://www.researchgate.net/publication/30022929_Multistage_Classification_for_Cardiovascular_Disease_Risk_Prediction.

(a) Template PPG signal with landmarks (b) Spline fitting on simulated components Spline fitting

METHOD AND SYSTEM FOR GENERATING SYNTHETIC TIME DOMAIN SIGNALS TO BUILD A CLASSIFIER

PRIORITY CLAIM

The present application claims priority from Indian patent application no. 202021018573, filed on Apr. 30, 2020. The entire contents of the aforementioned application are incorporated herein by reference.

TECHNICAL FIELD

The embodiments herein generally relates to synthetic data generation for classifiers and, more particularly, to a method and system for generating synthetic time domain signals to build a classifier.

BACKGROUND

Synthetic data generation has recently emerged as a substitution technique for handling the problem of bulk data needed in training machine learning algorithms. Healthcare, primarily cardiovascular domain is a major area where synthetic physiological data can be used to improve accuracy of the machine learning algorithms. Synthetic data is artificially generated data, used to mimic real world data while preserving some selected properties from the original data. This technique is argued by works in literature to be a more efficient way of getting labeled data for recognition as well as a mean to test performance of new software and scalability of Machine Learning (ML) techniques. A lot of research has been performed in the area of synthetic data generation in privacy community, speech processing and healthcare. Mostly, efficacy of the synthetic data are evaluated through improvement in machine learning (ML) techniques by introducing surrogate data in training sets.

SUMMARY

Embodiments of the present disclosure present technological improvements as solutions to one or more of the above-mentioned technical problems recognized by the inventors in conventional systems. For example, in one embodiment, a method for generating synthetic time domain signals to build a classifier is provided. The method receives a parent dataset of a plurality of samples of a time domain signal of interest comprising a combination of a class data and an non-class data.

Further identifies a plurality of subsets, from the parent dataset, corresponding to a plurality of morphological features identified for the time domain signal of interest, wherein each subset among the plurality of subset comprises p samples, wherein the plurality of morphological features comprise a Peak Sample (Ps), a Peak Amplitude (Pa), a Trough Sample (Ts), a Trough Amplitude (Ta), a Notch Sample (Ns), a Notch Amplitude (Na), a Dip Sample (Ds), a Dip Amplitude (Da), and distance between left and right samples corresponding to the 25%, 50%, 75% of the (Pa) defining distances $d_1$, $d_2$, $d_3$, and wherein the plurality of morphological features define a template for the time domain signal of interest.

Furthermore, processes each of the plurality of subsets corresponding to each of the plurality of morphological features to generate a plurality of sets of observational values with each of the plurality of sets of observational values comprising p actual values corresponding to each of the plurality of morphological features;

Furthermore, fits a gaussian kernel density estimate (KDE) to each of the plurality of sets of observational values;

Thereafter, generates N-point simulated data for each of the plurality of morphological features by generating N random samples from the gaussian KDE fitted to each of the plurality of sets of observational values; and Further constructs a plurality of synthetic time domain signals for the time domain signal of interest from the N-point simulated data for each of the plurality of morphological features in accordance to the template, wherein the constructing of the plurality of synthetic time domain signals includes:

a) determining a plurality of sequences derived from the generated N-point simulated data for each of the plurality of morphological features, wherein a plurality of elements in each of the plurality of sequences comprising Ts, Ps, Ds, Ns, $r_1$, $r_2$, $r_3$, $q_1$, $q_2$ and $q_3$, wherein values of $q_1$, $q_2$, $q_3$, $r_1$, $r_2$, $r_3$ are derived based on a preselected values of the distances $d_1$, $d_2$, $d_3$ defined for the template, and wherein position of each of the plurality of elements within each of the plurality of sequences is based on a set of conditions defined by a predefined set of morphological features among the plurality of morphological features;

b) generating from the plurality of sequences, a plurality of time domain signals corresponding to the time domain signal of interest by performing a spline fitting on each of the plurality of sequences, wherein the spline fitting utilizes piecewise linear regression to obtain parameters of lines connecting two successive elements among the plurality of elements of the each of the plurality of sequences;

c) smoothening each of the plurality of time domain signals using a smoothening technique to generate a plurality of smoothened time domain signals; and d) applying a peak smoothening technique on each of the smoothened plurality of time domain signals to construct the plurality of synthetic time domain signals for the time domain signal of interest.

Furthermore uses a combination of the plurality of samples in the parent dataset and the plurality of synthetic time domain signals as a training data for building a two stage cascaded classifier for classifying input data corresponding to time domain signal of interest into one of a class data and a non-class data, and wherein the two stage cascaded classifier comprises: a first classifier utilizing Matusita distance for likeness measurement and data explosion driven decision rule for classification; and a second classifier utilizing a random forest technique for classification. The first classifier classifies the input data as the non-class data and the class data with ambiguity, wherein the non-class data at an output of the first classifier is identified as a final non-class data; and the second classifier classifies the received class data with ambiguity into a final class data.

Thereafter utilizes the two stage cascaded classifier to validate the plurality of synthetic time domain signals.

Thereafter utilizes the two stage cascaded classifier build using the training data to test real time data corresponding to the time domain signal of interest and classify the real time data into the final class data and the final non-class data.

In another aspect, a system for generating synthetic time domain signals to build a classifier is provided. The system comprises a memory storing instructions; one or more Input/Output (I/O) interfaces; and one or more hardware processors coupled to the memory via the one or more I/O interfaces, wherein the one or more hardware processors are configured by the instructions to receive a parent dataset of a plurality of samples of a time domain signal of interest comprising a combination of a class data and an non-class data.

Further identify a plurality of subsets, from the parent dataset, corresponding to a plurality of morphological features identified for the time domain signal of interest, wherein each subset among the plurality of subset comprises p samples, wherein the plurality of morphological features comprise a Peak Sample (Ps), a Peak Amplitude (Pa), a Trough Sample (Ts), a Trough Amplitude (Ta), a Notch Sample (Ns), a Notch Amplitude (Na), a Dip Sample (Ds), a Dip Amplitude (Da), and distance between left and right samples corresponding to the 25%, 50%, 75% of the (Pa) defining distances $d_1$, $d_2$, $d_3$, and wherein the plurality of morphological features define a template for the time domain signal of interest.

Furthermore, process each of the plurality of subsets corresponding to each of the plurality of morphological features to generate a plurality of sets of observational values with each of the plurality of sets of observational values comprising p actual values corresponding to each of the plurality of morphological features;

Furthermore, fit a gaussian kernel density estimate (KDE) to each of the plurality of sets of observational values;

Thereafter, generate N-point simulated data for each of the plurality of morphological features by generating N random samples from the gaussian KDE fitted to each of the plurality of sets of observational values; and Further construct a plurality of synthetic time domain signals for the time domain signal of interest from the N-point simulated data for each of the plurality of morphological features in accordance to the template, wherein the constructing of the plurality of synthetic time domain signals includes:
  a) determine a plurality of sequences derived from the generated N-point simulated data for each of the plurality of morphological features, wherein a plurality of elements in each of the plurality of sequences comprising Ts, Ps, Ds, Ns, $r_1$, $r_2$, $r_3$, $q_1$, $q_2$ and $q_3$, wherein values of $q_1$, $q_2$, $q_3$, $r_1$, $r_2$, $r_3$ are derived based on a preselected values of the distances $d_1$, $d_2$, $d_3$ defined for the template, and wherein position of each of the plurality of elements within each of the plurality of sequences is based on a set of conditions defined by a predefined set of morphological features among the plurality of morphological features;
  b) generate from the plurality of sequences, a plurality of time domain signals corresponding to the time domain signal of interest by performing a spline fitting on each of the plurality of sequences, wherein the spline fitting utilizes piecewise linear regression to obtain parameters of lines connecting two successive elements among the plurality of elements of the each of the plurality of sequences;
  c) smoothen each of the plurality of time domain signals using a smoothening technique to generate a plurality of smoothened time domain signals; and
  d) apply a peak smoothening technique on each of the smoothened plurality of time domain signals to construct the plurality of synthetic time domain signals for the time domain signal of interest.

Furthermore use a combination of the plurality of samples in the parent dataset and the plurality of synthetic time domain signals as a training data for building a two stage cascaded classifier for classifying input data corresponding to time domain signal of interest into one of a class data and a non-class data, and wherein the two stage cascaded classifier comprises: a first classifier utilizing Matusita distance for likeness measurement and data explosion driven decision rule for classification; and a second classifier utilizing a random forest technique for classification. The first classifier classifies the input data as the non-class data and the class data with ambiguity, wherein the non-class data at an output of the first classifier is identified as a final non-class data; and the second classifier classifies the received class data with ambiguity into a final class data.

Thereafter utilize the two stage cascaded classifier to validate the plurality of synthetic time domain signals.

Thereafter utilize the two stage cascaded classifier build using the training data to test real time data corresponding to the time domain signal of interest and classify the real time data into the final class data and the final non-class data.

In yet another aspect, there are provided one or more non-transitory machine-readable information storage mediums comprising one or more instructions, which when executed by one or more hardware processors causes a method for generating synthetic time domain signals to build a classifier.

The method receives a parent dataset of a plurality of samples of a time domain signal of interest comprising a combination of a class data and an non-class data.

Further identifies a plurality of subsets, from the parent dataset, corresponding to a plurality of morphological features identified for the time domain signal of interest, wherein each subset among the plurality of subset comprises p samples, wherein the plurality of morphological features comprise a Peak Sample (Ps), a Peak Amplitude (Pa), a Trough Sample (Ts), a Trough Amplitude (Ta), a Notch Sample (Ns), a Notch Amplitude (Na), a Dip Sample (Ds), a Dip Amplitude (Da), and distance between left and right samples corresponding to the 25%, 50%, 75% of the (Pa) defining distances $d_1$, $d_2$, $d_3$, and wherein the plurality of morphological features define a template for the time domain signal of interest.

Furthermore, processes each of the plurality of subsets corresponding to each of the plurality of morphological features to generate a plurality of sets of observational values with each of the plurality of sets of observational values comprising p actual values corresponding to each of the plurality of morphological features;

Furthermore, fits a gaussian kernel density estimate (KDE) to each of the plurality of sets of observational values;

Thereafter, generates N-point simulated data for each of the plurality of morphological features by generating N random samples from the gaussian KDE fitted to each of the plurality of sets of observational values; and Further constructs a plurality of synthetic time domain signals for the time domain signal of interest from the N-point simulated data for each of the plurality of morphological features in accordance to the template, wherein the constructing of the plurality of synthetic time domain signals includes:
  a) determining a plurality of sequences derived from the generated N-point simulated data for each of the plurality of morphological features, wherein a plurality of elements in each of the plurality of sequences comprising Ts, Ps, Ds, Ns, $r_1$, $r_2$, $r_3$, $q_1$, $q_2$ and $q_3$, wherein values of $q_1$, $q_2$, $q_3$, $r_1$, $r_2$, $r_3$ are derived based on a preselected values of the distances $d_1$, $d_2$, $d_3$ defined for the template, and wherein position of each of the plurality of elements within each of the plurality of sequences is based on a set of conditions defined by a predefined set of morphological features among the plurality of morphological features;
b) generating from the plurality of sequences, a plurality of time domain signals corresponding to the time domain signal of interest by performing a spline fitting on each of the plurality of sequences, wherein the spline fitting utilizes piecewise linear regression to obtain parameters of lines connecting two successive elements among the plurality of elements of the each of the plurality of sequences;
c) smoothening each of the plurality of time domain signals using a smoothening technique to generate a plurality of smoothened time domain signals; and
d) applying a peak smoothening technique on each of the smoothened plurality of time domain signals to construct the plurality of synthetic time domain signals for the time domain signal of interest.

Furthermore uses a combination of the plurality of samples in the parent dataset and the plurality of synthetic time domain signals as a training data for building a two stage cascaded classifier for classifying input data corresponding to time domain signal of interest into one of a class data and a non-class data, and wherein the two stage cascaded classifier comprises: a first classifier utilizing Matusita distance for likeness measurement and data explosion driven decision rule for classification; and a second classifier utilizing a random forest technique for classification. The first classifier classifies the input data as the non-class data and the class data with ambiguity, wherein the non-class data at an output of the first classifier is identified as a final non-class data; and the second classifier classifies the received class data with ambiguity into a final class data.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

Figure 1:
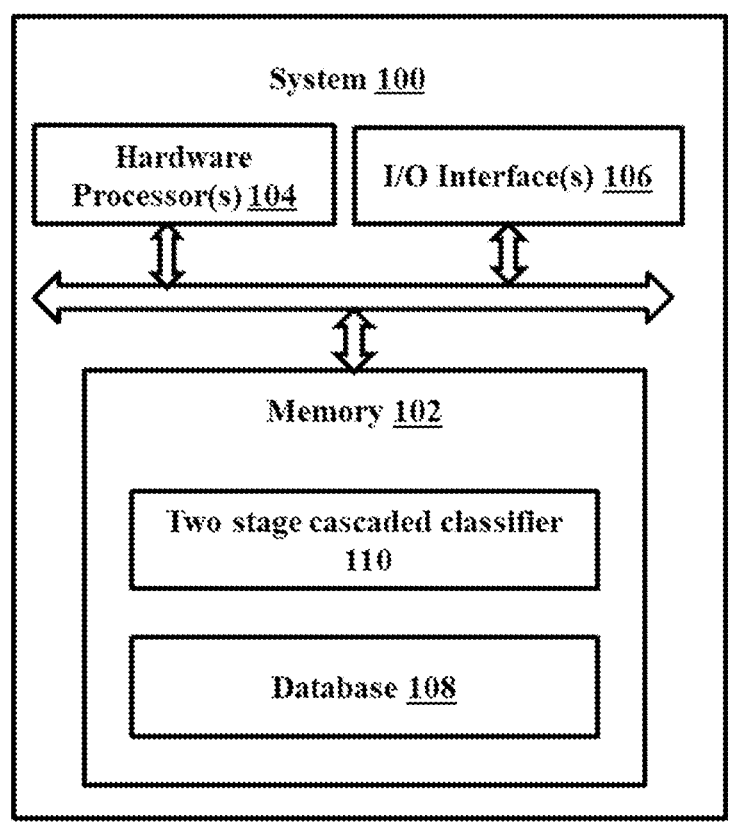
FIG. 1 is a functional block diagram of a system for generating synthetic time domain signals to build a classifier, in accordance with some embodiments of the present disclosure.

It should be appreciated by those skilled in the art that any block diagrams herein represent conceptual views of illustrative systems and devices embodying the principles of the present subject matter. Similarly, it will be appreciated that any flow charts, flow diagrams, and the like represent various processes which may be substantially represented in computer readable medium and so executed by a computer or processor, whether or not such computer or processor is explicitly shown.

DETAILED DESCRIPTION OF EMBODIMENTS

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the scope of the disclosed embodiments. It is intended that the following detailed description be considered as exemplary only, with the true scope being indicated by the following claims.

The physiological data or biosignals acquired from subjects being monitored are analyzed by health care systems to determine health condition of the subjects. Cardiac health care is emerging as a major area where synthetic physiological data like Photoplethysmogram (PPG), Electrocardiogram (ECG), Phonocardiogram (PCG), can be used improve accuracy of machine learning algorithm and help in early screening of various cardiovascular diseases like Coronary artery disease (CAD). CAD is caused due to plaque formation in coronary artery resulting in reduction in vessel diameter and may lead to heart attack or stroke. An early non-invasive detection or screening of CAD is an open area of research till date. PPG measures volumetric blood flow in capillaries over time and it has been very popular recently due to low cost implementation in wearables. Morphological attributes of PPG signal has been widely used in measurement of heart rate, blood pressure and in detection of several cardiac disease like CAD, arrythmia, atrial fibrilation, and the like in existing works. Significant research activities on characterization and analysis of PPG signal have been reported in recent years but research in synthetic PPG signal generation is limited. In terms of PPG signal generation, most significant approach has been stochastic modeling, where patient specific atlases of PPG signals were generated along with set of parameters that allows regeneration of statistically equivalent PPG signals by utilizing shape parameterization and a nonstationary model of PPG signal time evolution. However, these technique generate only patient specific PPG signatures and do not correlate with pathophysiological changes.

Embodiments herein provide a method and system for generating synthetic time domain signals to build a classifier, wherein the classifier is a two stage cascaded classifier. The time domain signal of interest can be any of the biosignals such as PPG, ECG and the like. Such synthetically generated time domain signals are then utilized as training dataset to build the two stage classifier. The generated two stage cascaded classifier is further utilized to classify the subjects into a class data (unhealthy subjects) and a non-class data (healthy subjects). The synthetic time domain signal generation approach provided by the method disclosed herein is explained in conjunction with synthetic generation of biosignal, with PPG signal as an example, and may not be construed as a limitation. Further, analysis of the synthetically generated PPG signals is performed to classify the subject associated with the PPG data, for example into a CAD class (unhealthy subjects) and a non-CAD class (healthy subjects). It can be understood that CAD and non-CAD is an example class and the classifier can be built and trained for classifying any class of interest. The method disclosed generates synthetic time domain signal of interest, such as the PPG, through statistical explosion. Initially, a parent dataset of actual samples of PPG data of CAD and non-CAD subjects is identified and statistical features (or morphological features) are extracted. Kernel density estimate (KDE) used to vary the feature distribution and create multiple data template from a single parent signal. PPG signal is again reconstructed from the distribution pattern using non-parametric techniques. The generated synthetic data set is used to build the two stage cascaded classifier to classify CAD (class) and non-CAD (non-class data).

Referring now to the drawings, and more particularly to FIGS. 1 through 4D, where similar reference characters denote corresponding features consistently throughout the figures, there are shown preferred embodiments and these embodiments are described in the context of the following exemplary system and/or method.

FIG. 1 is a functional block diagram of a system 100 for generating synthetic time domain signals to build a classifier, in accordance with some embodiments of the present disclosure.

In an embodiment, the system 100 includes a processor(s) 104, communication interface device(s), alternatively referred as input/output (I/O) interface(s) 106, and one or more data storage devices or a memory 102 operatively coupled to the processor(s) 104. The system 100, with the processor(s) is configured to execute functions of one or more functional blocks of the system 100.

Referring to the components of system 100, in an embodiment, the processor(s) 104, can be one or more hardware processors 104. In an embodiment, the one or more hardware processors 104 can be implemented as one or more microprocessors, microcomputers, microcontrollers, digital signal processors, central processing units, state machines, logic circuitries, and/or any devices that manipulate signals based on operational instructions. Among other capabilities, the one or more hardware processors 104 are configured to fetch and execute computer-readable instructions stored in the memory 102. In an embodiment, the system 100 can be implemented in a variety of computing systems including laptop computers, notebooks, hand-held devices such as mobile phones, personal digital Assistants (PDAs), cloud servers and the like.

The I/O interface(s) 106 can include a variety of software and hardware interfaces, for example, a web interface, a graphical user interface, and the like and can facilitate multiple communications within a wide variety of networks N/W and protocol types, including wired networks, for example, LAN, cable, etc., and wireless networks, such as WLAN, cellular, or satellite. In an embodiment, the I/O interface (s) 106 can include one or more ports for connecting a number of devices (nodes) of the system 100 to one another or to another server.

The memory 102 may include any computer-readable medium known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes. The memory 102 may comprise a two stage cascaded classifier 110 and other modules (not shown), to implement the functions for generating the synthetic time domain signals to build the classifier such as the two stage cascaded classifier 110.

Further, the memory 102 may include a database 108, which may store a parent dataset of a plurality of samples of a time domain signal of interest comprising a combination of a class data and an non-class data, a plurality of subsets, from the parent dataset, corresponding to a plurality of morphological features identified for the time domain signal of interest, N-point simulated data for each of the plurality of morphological features by generating N random samples from the gaussian KDE fitted to each of the plurality of sets of observational values, constructed a plurality of synthetic time domain signals for the time domain signal of interest from the N-point simulated data for each of the plurality of morphological features and so on.

Further, the two stage cascaded classifier 110 comprising a first classifier utilizing Matusita distance for likeness measurement and data explosion driven decision rule for classification and a second classifier utilizing random forest technique for classification. The two stage cascaded classifier 110 is explained in conjunction with FIG. 3.

Figure 2A:
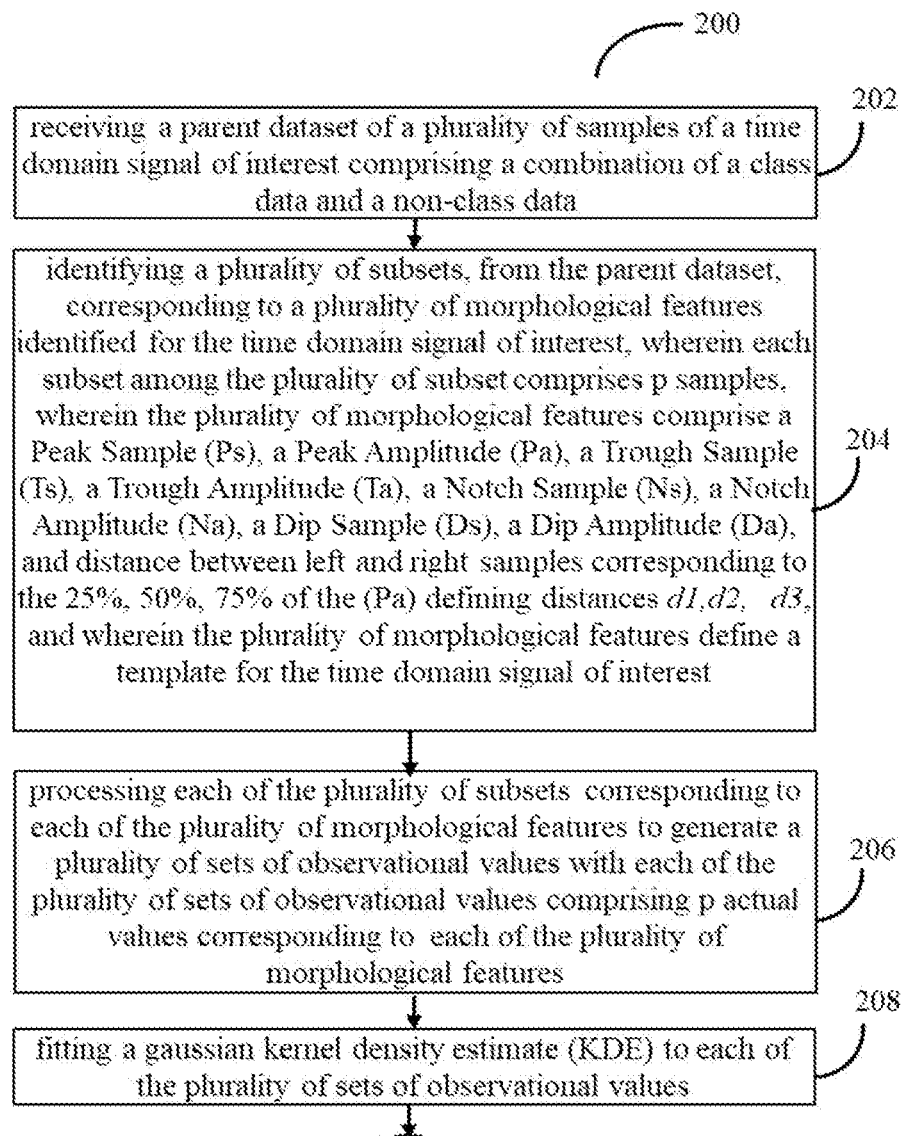
FIG. 2A depicts a first portion of a flow diagram illustrating a method for generating synthetic time domain signals to build the classifier using the system of FIG. 1.
Figure 2B:
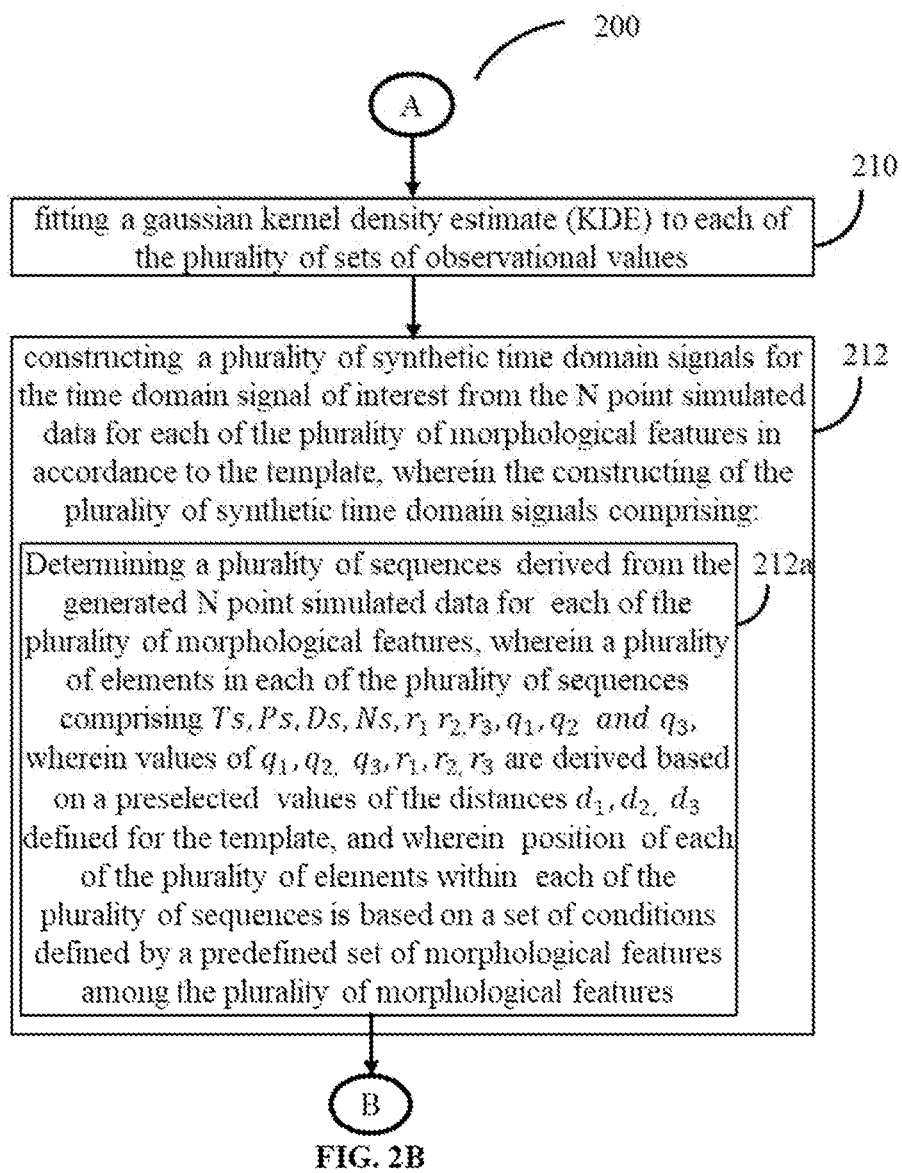
FIG. 2B depicts a second portion of a flow diagram illustrating a method for generating synthetic time domain signals to build the classifier using the system of FIG. 1.
Figure 2C:
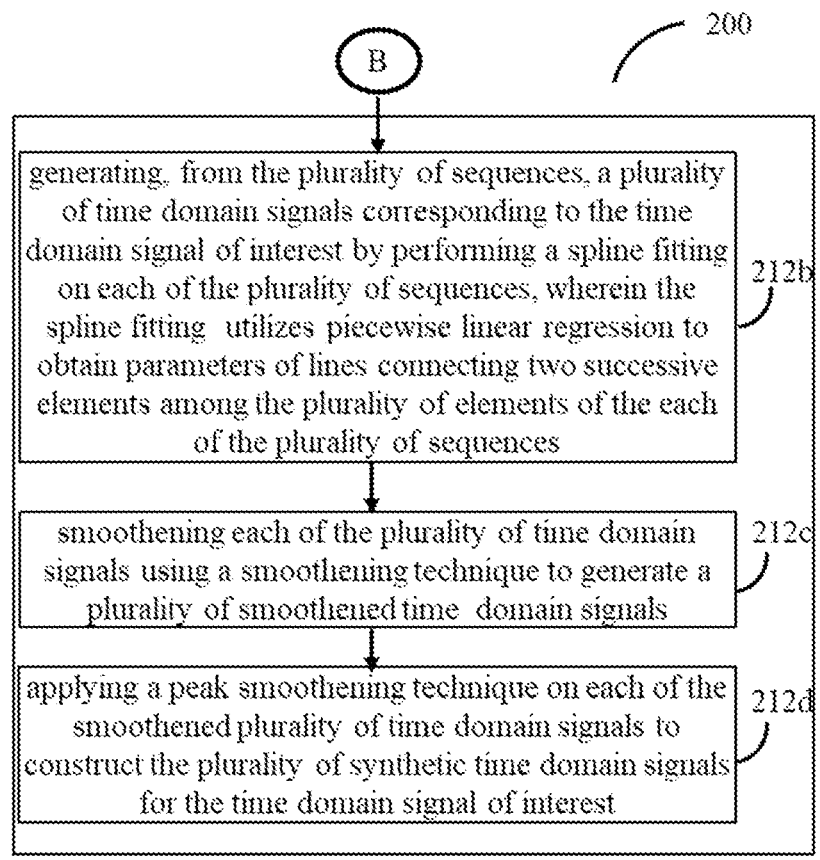
FIG. 2C depicts a third portion of a flow diagram illustrating a method for generating synthetic time domain signals to build the classifier using the system of FIG. 1.

Further, the memory 102 may comprise information pertaining to input(s)/output(s) of each step performed by the processor(s) 104 of the system and methods of the present FIGS. 2A, 2B and 2C depict a flow diagram illustrating a method for generating synthetic time domain signals to build the classifier using the system of FIG. 1, in accordance with some embodiments of the present disclosure.

In an embodiment, the database 108 may be external (not shown) to the system 100 and coupled to the system via the I/O interface 106. Functions of the components of system 100, for generating synthetic time domain signals to build the classifier, are explained in conjunction with FIGS. 2A through 4D.

FIGS. 2A, 2B and 2C depict a flow diagram illustrating a method for generating synthetic time domain signals to build the classifier using the system of FIG. 1, in accordance with some embodiments of the present disclosure.

Figure 3:
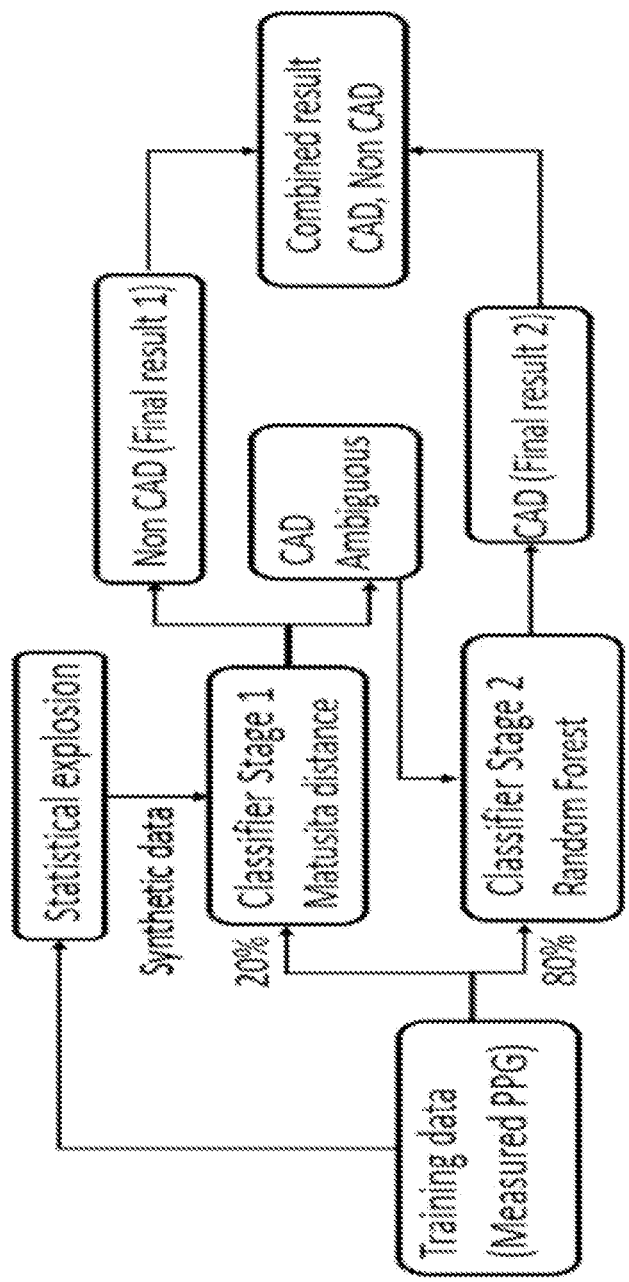
FIG. 3 illustrates architectural overview of the classifier of the system of FIG. 1, wherein the classifier is a two stage cascaded classifier, in accordance with some embodiments of the present disclosure.

In an embodiment, the system 100 comprises one or more data storage devices or the memory 102 operatively coupled to the processor(s) 104 and is configured to store instructions for execution of steps of the method 200 by the processor(s) or one or more hardware processors 104. The steps of the method 200 of the present disclosure will now be explained with reference to the components or blocks of the system 100 as depicted in FIG. 1 and FIG. 3 and the steps of flow diagram as depicted in FIGS. 2A through 2C. Although process steps, method steps, techniques or the like may be described in a sequential order, such processes, methods and techniques may be configured to work in alternate orders. In other words, any sequence or order of steps that may be described does not necessarily indicate a requirement that the steps to be performed in that order. The steps of processes described herein may be performed in any order practical. Further, some steps may be performed simultaneously.

Referring now to the steps of the method 200, at step 202, one or more hardware processors 104 are configured to receive the parent dataset of a plurality of samples of a time domain signal of interest comprising a combination of a class data and n non-class data. For an example parent dataset can include PPG signals of 145 subjects, which are actual recorded signals at a hospital, using non-medical grade commercial pulse oximeter (CMS 50D+) at a sampling rate of 60 Hz.

This dataset serves as the parent PPG dataset for subsequent analysis and comprises of 90 CAD and 55 non CAD subjects, annotated using Angiogram report. The dataset ensures a wide variation in patient demography along with different pathological conditions for non-CAD patients and also varying percentage level of heart blockages for CAD patients.

Figure 4A:
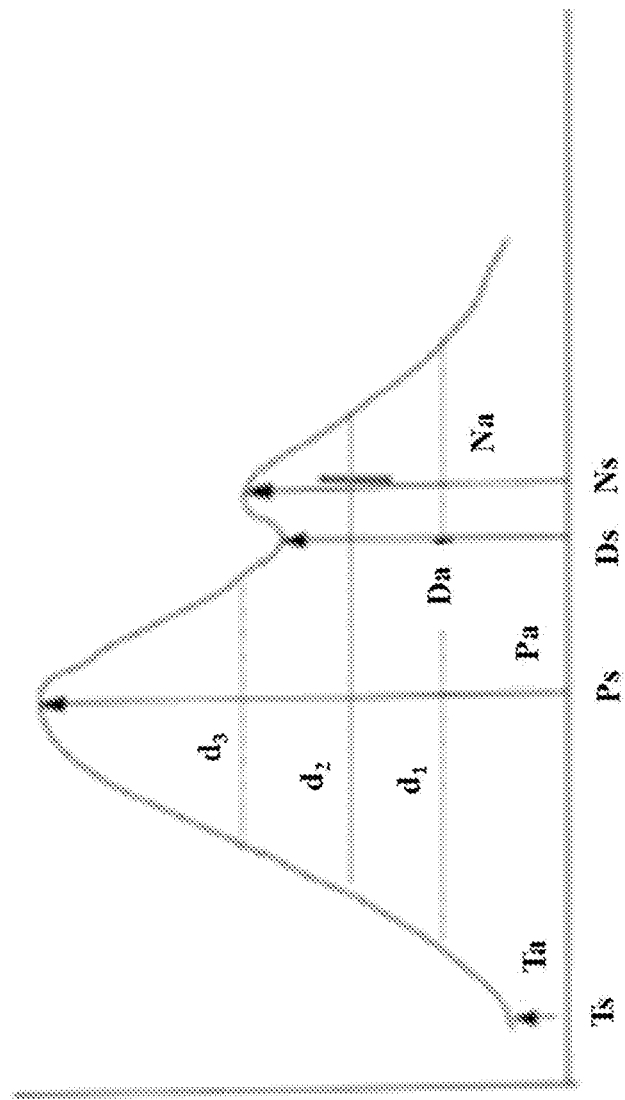
FIG. 4A depicts a template PPG signal (time domain signal) with landmarks for feature distribution, in accordance with some embodiments of the present disclosure.

At step 204 of the method 200, the one or more hardware processors 104 are configured to identify a plurality of subsets, from the parent dataset, corresponding to a plurality of morphological features identified for the time domain signal of interest. Each subset among the plurality of subset comprises p samples and the plurality of morphological features comprise a Peak Sample (Ps), a Peak Amplitude (Pa), a Trough Sample (Ts), a Trough Amplitude (Ta), a Notch Sample (Ns), a Notch Amplitude (Na), a Dip Sample (Ds), a Dip Amplitude (Da), and distance between left and right samples corresponding to the 25%, 50%, 75% of the (Pa) providing distances $d_1$, $d_2$, $d_3$. The morphological features mentioned above are for a PPG signal, however, for any time domain signal these features can be as identified by a subject matter expert. These identified features capture the most important and relevant information in the signal, which would be critical in classifying the time domain signal of interest into the relevant classes. The plurality of morphological features define a template for the time domain signal of interest as depicted in FIG. 4A, used for generating the synthetic time domain signals. FIG. 4A depicts the template PPG signal (time domain signal) with landmarks for feature distribution, in accordance with some embodiments of the present disclosure.

Thus, from the parent data set of PPG signals in the database 108, certain morphological landmarks (also referred as the plurality of morphological features) are annotated as shown in FIG. 4A. Depicted are the morphological features or landmarks such as the Peak Sample (Ps), the Peak Amplitude (Pa), the Trough Sample (Ts), the Trough Amplitude (Ta), the Notch Sample (Ns), the Notch Amplitude (Na), the Dip Sample (Ds), the Dip Amplitude (Da), and the distance between left and right samples corresponding to the 25%, 50%, 75% of Pa providing the distances $d_1$, $d_2$, $d_3$, where 'left' means the position before Ps, and 'right' means the position after the Ps. So in total there are eleven features.

At step 206 of the method 200, the one or more hardware processors 104 are configured to process each of the plurality of subsets corresponding to each of the plurality of morphological features to generate a plurality of sets of observational values with each of the plurality of sets of observational values comprising p actual values corresponding to each of the plurality of morphological features.

At step 208 of the method 200, the one or more hardware processors 104 are configured to fit a gaussian kernel density estimate (KDE) to each of the plurality of sets of observational values.

At step 210 of the method 200, the one or more hardware processors 104 are configured to generate N-point simulated data for each of the plurality of morphological features by generating N random samples from the gaussian KDE fitted to each of the plurality of sets of observational values.

The mathematical analysis for the steps 206 through 210 is explained below.

Several cycles are given for each morphological feature, interchangeably referred herein as component. Let the number of cycles be p. For data explosion, first step is to simulate each of the eleven components. In order to do so, the observations or observation values related to component $X=x_i$, $i=1, 2, 3 \ldots p$. A probability density function using a gaussian kernel density estimate (KDE) is fitted to the $x_i$-s. 'Bandwidth' parameter of KDE algorithm affects the smoothness of the resulting curve. Mathematically, a kernel is a positive function K (x, h), which is controlled by the bandwidth parameter h. Given this kernel form, the density estimate at a point y within a group of points $x_i$, $i=1, 2, x_i 3 \ldots p$ is given by: $\rho_K(y) = \Sigma_{i=1}^{P} K[(y-x_i)/h]$. A gaussian kernel is of the form $$K(x, h) = \exp\left(\frac{x^2}{2h^2}\right).$$

Now, suppose X is to be simulated, say N times. This is equivalent to drawing N random samples from kernel density. In order to do so, N random samples are drawn from $x_1$, $x_2 \ldots x_p$ with replacement. Let the samples be denoted by $samp_N$. This constitutes the mean of the kernel density. Then N random samples are drawn from the kernel N ($samp_N$,h). This constitutes the simulated data. This process is repeated for each of the eleven components or the morphological features.

At step 212 of the method 200, the one or more hardware processors 104 are configured to construct a plurality of synthetic time domain signals for the time domain signal of interest from the N-point simulated data for each of the plurality of morphological features in accordance to the template, wherein the constructing of the plurality of synthetic time domain signals comprises:

a) Determining (212a) a plurality of sequences derived from the generated N-point simulated data for each of the plurality of morphological features, wherein a plurality of elements in each of the plurality of sequences comprising Ts, Ps, Ds, Ns, $r_1$ $r_2$, $r_3$, $q_1$, $q_2$ and $q_3$ wherein values of $q_1$, $q_2$, $q_3$, $r_1$, $r_2$, $r_3$ are derived based on the distances $d_1$, $d_2$, $d_3$ defined for the template. Position of each of the plurality of elements within each of the plurality of sequences is based on a set of conditions defined by a predefined set of morphological features among the plurality of morphological features.

b) Generating (212b), from the plurality of sequences, a plurality of time domain signals corresponding to the time domain signal of interest by performing a spline fitting on each of the plurality of sequences, wherein the spline fitting utilizes piecewise linear regression to obtain parameters of lines connecting two successive elements among the plurality of elements of the each of the plurality of sequences.

c) Smoothening (212c) each of the plurality of time domain signals using a smoothening technique to generate a plurality of smoothened time domain signals.

d) Applying (212d) a peak smoothening technique on each of the smoothened plurality of time domain signals to construct the plurality of synthetic time domain signals for the time domain signal of interest.

The mathematical representation of steps 212a through 212d is explained below with case examples below. Thus, based on the simulated data for eleven components, required is to construct the entire signal. To do that, the first thing is to specify the sample point regarding the 25%, 50%, and 75% of Pa ($d_1$, $d_2$, and $d_3$) at both sides of Ps. Thus, the required is to determine the positions of Pa/4; Pa/ and 3Pa/4 before and after Ps. Suppose the, sample points corresponding to Pa/2 are $q_1$ and $r_1$ before and after Ps, respectively.

Figure 4B:
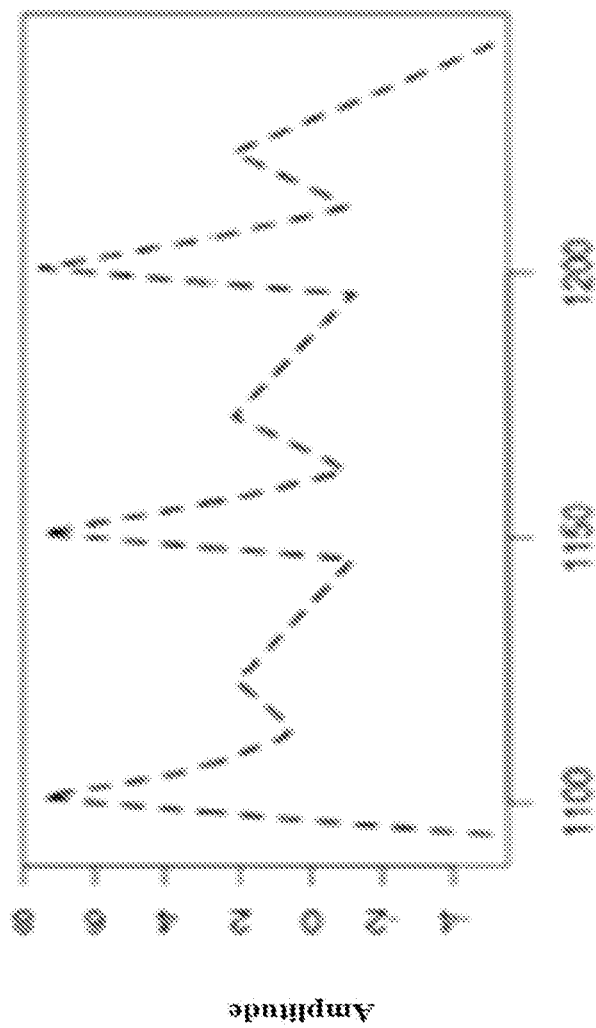
FIG. 4B depicts a reconstructed signal from the feature distribution, in accordance with some embodiments of the present disclosure.
Figure 4C:
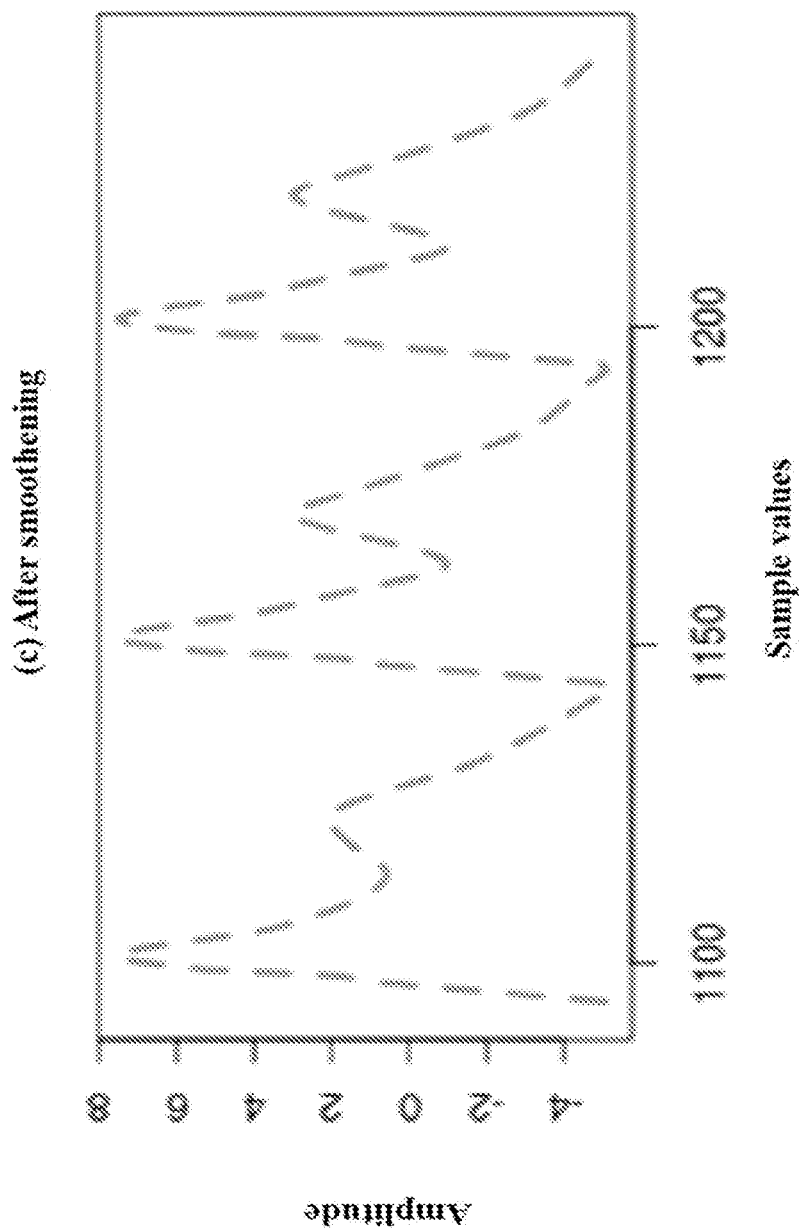
FIG. 4C depicts a reconstructed signal after applying a smoothening technique on the signal reconstructed from the feature distribution, in accordance with some embodiments of the present disclosure.
Figure 4D:
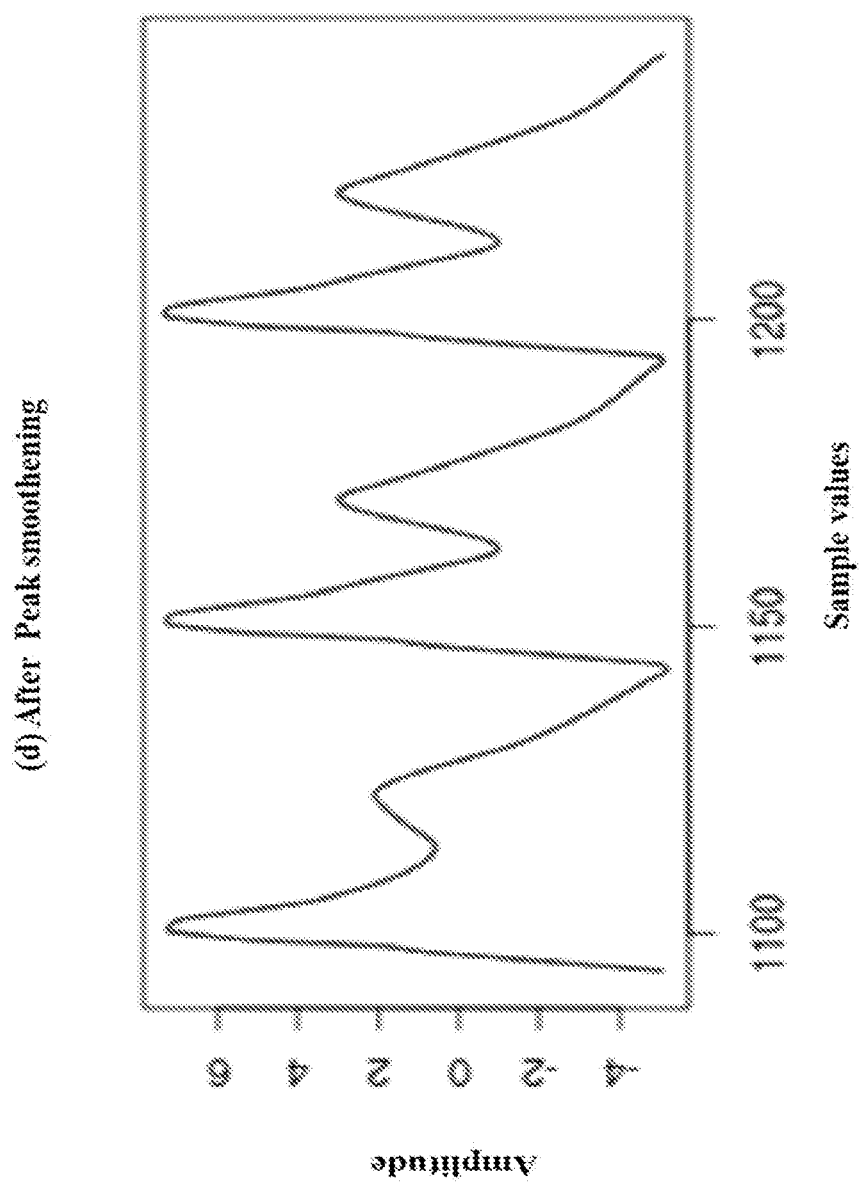
FIG. 4D depicts a reconstructed signal (synthetic time domain signal) after applying a peak smoothening technique on the smoothened signal, in accordance with some embodiments of the present disclosure.

Deriving values of $q_1$, $q_2$, $q_3$, $r_1$, $r_2$, $r_3$ based on $d_1$, $d_2$, and $d_3$: As can be seen from FIG. 4A $d_1$, $d_2$, and $d_3$ are distances between two points on the PPG template of FIG. 4A. Given or identified is a value $d_1$, which is equal to $r_1-q_1$. Similarly value of $d_2$ is identified and is equal to and same follows for $d_3$, which is equal to $r_3-q_3$ Now, from the starting point, i.e. trough sample Ts, an initial $q_1$ is determined by unitary method, with comparison to Pa and $q_2$ and $q_3$ corresponding to l=2 and 3l=4 are determined similarly by unitary method; l being the signal width. Once $q_1$ $q_2$, and $q_3$ are determined then, $r_1$, $r_2$, and $r_3$ can be derived from $d_1$, $d_2$, and $d_3$ Determining position of each of the plurality of elements within each of the plurality of sequences is based on a set of conditions defined by the predefined set of morphological features: It is critical while selecting values of $r_2$ and $r_1$. The values can fall before or after the dip sample Ds. To check this, Pa/2 is compared with dip amplitude Da. If Pa/2>Da, that means $r_2$ is placed either before Ds, or between Ds and Ns, or after Ns. The first situation will happen if $r_2=q_2+d_2<$Ds, the second situation will happen if Ds$<r_2=q_2+d_2<$Ns and the third situation will happen if $r_2=q_2+d_2>$Ns. If the first situation (a condition among a first set happens for both $r_1$ and $r_2$ then the sequence of sample points or elements in the simulated density would be Ts, $q_1$, $q_2$, $q_3$, Ps, $r_3$, $r_2$, $r_1$, Ds, Ns along with their amplitudes. If the first situation happens for $r_2$ and the second situation happens for $r_1$ then the sequence of sample points in the simulated density would be Ts, $q_1$, $q_2$, $q_3$, Ps, $r_2$, $r_3$, Ds, $r_1$, Ns along with their amplitudes, and the process goes on similarly for other situations. In total, there are nine possibilities along with corresponding sequences. However, if Pa/2<Da that will imply Pa/4<P/2<Da. In that case both $r_1$ and $r_2$ will be greater than Ns. Then the sequence of sample points in the simulated density would be Ts, $q_1$, $q_2$, $q_3$, Ps, $r_3$, Ds, Ns, $r_2$, $r_1$ along with their amplitudes. Similarly we can construct the case when Pa/4<Da<Pa/2. Depending on the sequence of sample points arranged along with respective amplitudes. These sample points are then connected using spline, i.e., each point is connected by a different line, the parameters of the line being selected by a piecewise linear regression process. We now smooth the curve using the smoothening technique such as 'a LOESS function' to smooth the curve. At each point in the data a linear parametric function is fir to a subset of the data, with explanatory variable values near the point whose response is being estimated. the neighborhood is determined by the nearest neighbor approach using a smoothing parameter $\alpha=\frac{1}{3}$, which the fraction of the total data points to be used in the local fitting. A polynomial is fit using the gaussian weight function $$w(x, x_0) = \exp\left(-\frac{(x-x_0)^2}{2h^2}\right),$$

where $x_0$ is the point in the data-set around which the polynomial to be fitted, and x is an arbitrary point in its neighborhood, and h is the bandwidth around which the local neighborhood is formed. Thus, the weight function assigns more weight to points near the point whose response is being estimated and less weight to points further away. Thus, instead of using the least squares, the following function is minimized: $\Sigma_{i=1}{}^n \Sigma_{j \in \mathcal{N}_i} w(x_j,x_i)(Y_j-[\beta_0+\beta_1(x_i-x_j)])^2$, where Y is the corresponding value on the fitted polynomial around xi, $\mathcal{N}_i$ is the neighborhood around $x_i$. $\beta_0$ and $\beta_1$ are unknown parameters to be estimated. To smooth out the reconstructed signal, backward step wise regression technique is applied in a small neighborhood of the peak. FIG. 4B depicts a reconstructed signal from the feature distribution, FIG. 4C depicts a reconstructed signal after applying a smoothening technique on the signal reconstructed from the feature distribution and FIG. 4D depicts a reconstructed signal (synthetic time domain signal) after applying a peak smoothening technique on the smoothened signal, in accordance with some embodiments of the present disclosure. FIGS. 4B, 4C and 4D shows the three phases of signal reconstruction.

FIG. 3 illustrates architectural overview of the classifier of the system of FIG. 1, wherein the classifier is the two stage cascaded classifier 110, in accordance with some embodiments of the present disclosure. A combination of the plurality of samples in the parent dataset and the plurality of synthetic time domain signals is used as a training data for building the two stage cascaded classifier 110 for classifying input data corresponding to time domain signal of interest into one of the class data and the non-class data. The two stage cascaded classifier comprises a first classifier utilizing Matusita distance for likeness measurement and data explosion driven decision rule for classification; and a second classifier utilizing one of a random forest technique and a Support Vector Machines (SVM) for classification. The first classifier classifies the input data as the non-class data and the class data with ambiguity. The non-class data at an output of the first classifier is identified as a final non-class data and the second classifier classifies the received class data with ambiguity into a final class data.

Thus, as can be seen in FIG. 3, the generated synthetic data set is used to classify CAD (class data) and non-CAD (non-class data) through a cascaded classifier. In the first stage, statistical features extracted from the synthetically populated data set is used to differentiate between CAD and non CAD using a rule based on 'Matusita distance'. This classifier is inherently biased towards identifying non-CAD data (time series signal). Results from Stage 1 are again run through Stage 2, exploiting similar statistical features and a standard classifier like the SVM or the Random Forest. Stage 2 provides better classification of CAD cases. Thus, the cascading architecture provided by the method disclosed along with the training data sets builds a classifier such that it corrects the bias inherent in any binary classification procedure towards one class or another, and produces better classification results as compared to the conventional techniques. The two stage cascaded classifier 110, once built using the training dataset as in FIG. 3, can then be used for to test real time data of subjects being monitored for corresponding to the time domain signal of interest such as PPG and classify the real time data into the final class data (CAD subjects) and the final non-class data (non-CAD subjects).

Stage 1 (first classifier)—For the 1st stage classifier, from the parent data set of 90 CAD and 55 non CAD data, we keep 45 CAD and 28 non-CAD (50%) observations as test data. From rest of the data serving as 'training set', 9 CAD and 6 non-CAD data are taken, (i.e. about 20%) and inflate them (1000 for each observation) using synthetic PPG generation technique as discussed by the method disclosed herein. For aiding in classification, 13 statistical features are extracted from each of the simulated data (timeseries). These features contain important statistical information regarding inherent properties of a signal, that may help in discriminating a healthy subject from a diseased one. Features are calculated on both raw time series data as well as timeseries after de-trending and de-seasonalizing (TSA) for a precise and comprehensive calibration. The methodology of feature extraction follows the path as in one of the works in literature. Features used are: Trend (TSA), Seasonality (TSA), Serial Correlation (TSA), Nonlinearity (raw and TSA), Skewness(raw and TSA), Kurtosis(raw and TSA), Self-similarity (raw), Periodicity (raw), Average Maharaj distance (raw) and number of direction changes (raw). There are 13 features both for CAD and non-CAD patients. Suppose the i-th feature in CAD and non-CAD is denoted as $\mathcal{F}_i^C$ and $\mathcal{F}_i^{NC}$ respectively where i=1, 2, . . . 13. A non-parametric density function can be fit to both of them using kernel density estimation, using Gaussian kernel. Thus, two distributions are fir say as $f_i^C$ to $\mathcal{F}_i^C$ and as $f_i^{NC}$ to $\mathcal{F}_i^{NC}$. To discriminate CAD and non-CAD features, similarity between $f_i^C$ and $f_i^{NC}$ needs to be calculated. This necessitates a measure of similarity between two distributions, and the Matusita distance in measuring the likeness, or lack of it, between $f_i^C$ and $f_i^{NC}$. For two kernel density estimates, say P and Q respectively, where d observable points for each density are available, the Matusita distance is $d=\Sigma_{j=1}^d(\sqrt{P_j}-\sqrt{Q_j})^2=2-2\Sigma_{j=1}^d(\sqrt{P_jQ_j})$. The distance lies between 0 and 2. A value near 0 means high similarity, and a high value signifies the opposite. Those features for which the Matusita distance between CAD and non-CAD density is more than 1 is accepted. By this process, the number of features are reduced to 11. or a real-life non-CAD signal, 9 out of 11 features tally with their corresponding non-CAD distributions most of the time. For a real-life CAD signal, 5 (sometimes 6) features tally with their corresponding CAD distributions most of the time. Based on these observations, a 'Majority rule' is defined, i.e. if the extracted feature set of a new data has the above-mentioned (or 6) members corresponding with the CAD distribution, classify this as CAD. If 9 members out of 11 correspond with the non-CAD distribution, classify the new data as non-CAD. If none of the above two scenario holds, then go further analysis is performed. Using the above thumb rule on the test data, we have the following result: out of 45 CAD data, it can correctly classify 30 observations, and mistakenly assigns 8 observations to the non-CAD class. For 7 other observations, the rule cannot decide anything. The performance is much better for a non-CAD case. Out of 28 healthy subjects, it can correctly classify 23, i.e. 82% as non-CAD. It mistakes only for 2 cases, and for the other 3, the decision remains ambiguous.

Result as in Confusion Matrix for Stage 1

|  | CAD | Non-CAD | others |
| --- | --- | --- | --- |
| CAD | 30 | 8 | 7 |
| Non-CAD | 2 | 23 | 3 |

Stage 2 (second classifier): Stage 1 shows that the data explosion driven decision rule is more effective in identifying a non-CAD than a CAD method. So, if the decision rule assigns an observation as non-CAD, it is labeled as non-CAD. The rest of the observations are sent to stage 2. That means, 31 observations (23 correctly and 8 wrongly identified as non-CAD) are assigned as non-CAD (as shown in Confusion matrix for stage 1). There are more observations in the test data, which were classified either as CAD or as ambiguous. Note that we have used only about 20% of the training data in stage 1. 36 CAD and 21 non-CAD observations still remain unused. Eleven statistical features are extracted from these remaining training data in the same way as above. Then a standard classifier is run on its features and applied is the learning on the 42 test observations, belonging to CAD and 'other' class (Confusion matrix stage 1) at the second stage. Also note that 20% training data used in stage 1 is not mixed with the rest 80%, because they could not provide a definitive solution for the 42 test observations in stage 1. Though some of them are identified as CAD, this needs further evaluation. Hence using the previous 20% again may jeopardize the result. Different classification techniques are tried, and it is observed that a random forest with 50 tree works best at the second stage.

Result as in Confusion Matrix for Stage 2

|  | CAD | Non-CAD |
| --- | --- | --- |
| CAD | 35 | 2 |
| Non-CAD | 2 | 3 |

Combining this classification result with that found in stage 1, the final classification:

Combined Confusion Matrix:

|  | CAD | Non-CAD |
| --- | --- | --- |
| CAD | 35 | 2 |
| Non-CAD | 2 | 3 |

The reason for combining the result is that, it is always of higher importance to correctly identify CAD patients. However, most of the real-life classifiers are heavily biased towards one class or another depending on which class has more patients. The two stage cascaded classifier by the method disclosed here corrects the bias in a sense that each of the stages complements the other. The first stage performs better in identifying a non-CAD patient since the feature alignment is more definitive for non-CAD cases. The second stage performs better in identifying a CAD patient since more CAD observations are present in the training data, and hence learning is better there. In this sense, the biases at both sides are checked, and we have a balanced result.

RESULT: The two stage cascaded classifier is compared with a number of classifiers. A consider straightforward classification is considered, which can be any one of two—a decision rule based on the feature alignment as discussed in stage 1, where the entire training data set is inflated by synthetic generation; and a classifier directly learning from the extracted features on the entire training data. In other words, we compare the method disclosed herein, with cases where only stage 1 case, framing the decision rule is pretty straightforward. For the second case, the stage 2 is compared straightforward with classification where Random forest (RF) is used directly on the training data (this is because random forest is used in stage 2). Six methods are compared—two stage classifier with random forest at the second stage, decision rule based on data inflation, random forest on the entire training data, and SVM with gaussian kernel on the entire training data, and two prior works. Results are shown in Table 1.

As indicated from other conventional classifiers in overall classification results, the nearest performer is SVM with gaussian kernel. Though the inflation-based decision rule has high specificity, its sensitivity, and hence False Positive Rate (FPR), is very low, and hence it cannot be considered a good performer for detecting CAD. Note that conventional measures of classification performances are minimum (precision, recall), or the average of True Positive Rate (TPR) (i.e. precision) and FPR. Inflated technique has not been used on the entire data set, rather, we inflate only a small amount of data to make a rule engine, and run a conventional classifier on the rest of the data. Reason for that is the PPG simulation uses an underlying distributional assumption, from which the simulated data arises. Since the underlying distribution remains the same for a patient, the simulated data, and hence the extracted features do not induce much variety; any decision rule based on them will overfit.

TABLE 1

|  | Sensitivity | Specificity | Precision | TNR |
|---|---|---|---|---|
| 2 stage cascaded classifier | 0.78 | 0.93 | 0.95 | 0.72 |
| Inflation | 0.62 | 0.86 | 0.88 | 0.59 |
| RF | 0.73 | 0.68 | 0.79 | 0.61 |
| SVM | 0.78 | 0.79 | 0.86 | 0.69 |
| Prior art 1 | 0.51 | 0.69 | 0.72 | 0.62 |
| Prior art 2 | 0.75 | 0.73 | 0.69 | 0.72 |

Thus, the method provides approach to generate synthetic biosignals such as PPG signal and uses the synthetic data to better build a classifier the signal to better classify CAD subjects in real time or with test data and hence is a potential tool to screen CAD patients. Synthetic data generation coupled with the 2 stage classifier can also be used as a generic framework to improve machine learning accuracy for any time series signal.

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

It is to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g. any kind of computer like a server or a personal computer, or the like, or any combination thereof. The device may also include means which could be e.g. hardware means like e.g. an application-specific integrated circuit (ASIC), a field-programmable gate array (FPGA), or a combination of hardware and software means, e.g. an ASIC and an FPGA, or at least one microprocessor and at least one memory with software processing components located therein. Thus, the means can include both hardware means, and software means. The method embodiments described herein could be implemented in hardware and software. The device may also include software means. Alternatively, the embodiments may be implemented on different hardware devices, e.g. using a plurality of CPUs.

The embodiments herein can comprise hardware and software elements. The embodiments that are implemented in software include but are not limited to, firmware, resident software, microcode, etc. The functions performed by various components described herein may be implemented in other components or combinations of other components. For the purposes of this description, a computer-usable or computer readable medium can be any apparatus that can comprise, store, communicate, propagate, or transport the program for use by or in connection with the instruction execution system, apparatus, or device.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope of disclosed embodiments being indicated by the following claims.

What is claimed is:

1. A processor implemented method for generating synthetic time domain signals to build a classifier, the method comprising:

receiving, by one or more hardware processors, a parent dataset of a plurality of samples of a time domain signal of interest comprising a combination of a class data, wherein the class data refer to a subject with Coronary artery disease, CAD and a non-class data, wherein the non-class data refer to the subject without the CAD;

identifying, by the one or more hardware processors, a plurality of subsets, from the parent dataset, corresponding to a plurality of morphological features identified for the time domain signal of interest, wherein each subset among the plurality of subsets comprises p samples corresponding to the plurality of the morphological features, further wherein the plurality of morphological features comprise a Peak Sample (Ps), a Peak Amplitude (Pa), a Trough Sample (Ts), a Trough Amplitude (Ta), a Notch Sample (Ns), a Notch Amplitude (Na), a Dip Sample (Ds), a Dip Amplitude (Da), and distance between left and right samples corresponding to the 25%, 50%, 75% of the (Pa) defining distances $d_1$, $d_2$, $d_3$, and wherein the plurality of morphological features define a template for the time domain signal of interest;

processing, by the one or more hardware processors, each of the plurality of subsets corresponding to each of the plurality of morphological features to generate a plurality of sets of observational values with each of the plurality of sets of observational values comprising p actual values corresponding to each of the plurality of morphological features;

fitting, by the one or more hardware processors, a gaussian kernel density estimate (KDE) to each of the plurality of sets of observational values;

generating, by the one or more hardware processors, N-point simulated data for each of the plurality of morphological features by generating N random samples from the gaussian KDE fitted to each of the plurality of sets of observational values;

constructing, by the one or more hardware processors, a plurality of synthetic time domain signals for the time domain signal of interest from the N-point simulated data for each of the plurality of morphological features in accordance to the template, wherein the constructing of the plurality of synthetic time domain signals comprising:

determining a plurality of sequences derived from the generated N-point simulated data for each of the plurality of morphological features, wherein a plurality of elements in each of the plurality of sequences comprising Ts, Ps, Ds, Ns, $r_1$ $r_2$, $r_3$, $q_1$, $q_2$ and $q_3$, wherein values of $q_1$, $q_2$, $q_3$, $r_1$, $r_2$, $r_3$ are derived based on a preselected values of the distances $d_1$, $d_2$, $d_3$ defined for the template, and wherein position of each of the plurality of elements within each of the plurality of sequences is based on a set of conditions defined by a predefined set of morphological features among the plurality of morphological features;

generating, from the plurality of sequences, a plurality of time domain signals corresponding to the time domain signal of interest by performing a spline fitting on each of the plurality of sequences, wherein the spline fitting utilizes piecewise linear regression to obtain parameters of lines connecting two successive elements among the plurality of elements of the each of the plurality of sequences;

smoothening each of the plurality of time domain signals using a smoothening technique to generate a plurality of smoothened time domain signals; and applying a peak smoothening technique on each of the smoothened plurality of time domain signals to construct the plurality of synthetic time domain signals for the time domain signal of interest; and building, via the one or more hardware processors, a two stage cascaded classifier for classifying input data corresponding to the time domain signal of interest into one of the class data and the non-class data by using a combination of the plurality of samples in the parent dataset and the plurality of synthetic time domain signals as a training data, and wherein the two stage cascaded classifier comprises:

a first classifier utilizing Matusita distance for likeness measurement and data explosion driven decision rule for classification, wherein a plurality of statistical features is extracted from the plurality of synthetic time domain signals to differentiate between the class data and the non-class data, using a rule based on the Matusita distance; and a second classifier utilizing a random forest technique for classification, wherein constructing the two stage cascaded classifier using the training data is used to correct bias, test real time data corresponding to the time domain signal of interest and classify the real time data into the final class data and the final non-class data.

2. The method as claimed in claim 1, wherein the first classifier classifies the input data as the non-class data and the class data with ambiguity, wherein the non-class data at an output of the first classifier is identified as a final non-class data, and the second classifier classifies the received class data with ambiguity into a final class data.

3. The method as claimed in claim 1, wherein the two stage cascaded classifier is used to validate the plurality of synthetic time domain signals.

4. The method as claimed in claim 1, wherein the time domain signal of interest is a biosignal.

5. A system for generating synthetic time domain signals to build a classifier, the system comprising:

a memory storing instructions;

one or more Input/Output (I/O) interfaces; and one or more hardware processors coupled to the memory via the one or more I/O interfaces, wherein the one or more hardware processors are configured by the instructions to:

receive a parent dataset of a plurality of samples of a time domain signal of interest comprising a combination of a class data, wherein the class data refer to a subject with Coronary artery disease, CAD and a non-class data, wherein the non-class data refer to the subject without the CAD;

identify a plurality of subsets, from the parent dataset, corresponding to a plurality of morphological features identified for the time domain signal of interest, wherein each subset among the plurality of subset comprises p samples corresponding to the plurality of the morphological features, wherein the plurality of morphological features comprise a Peak Sample (Ps), a Peak Amplitude (Pa), a Trough Sample (Ts), a Trough Amplitude (Ta), a Notch Sample (Ns), a Notch Amplitude (Na), a Dip Sample (Ds), a Dip Amplitude (Da), and distance between left and right samples corresponding to the 25%, 50%, 75% of the (Pa) defining distances $d_1$, $d_2$, $d_3$, and wherein the plurality of morphological features define a template for the time domain signal of interest;

process each of the plurality of subsets-corresponding to each of the plurality of morphological features to generate a plurality of sets of observational values with each of the plurality of sets of observational values comprising p actual values corresponding to each of the plurality of morphological features;

fit a gaussian kernel density estimate (KDE) to each of the plurality of sets of observational values;

generate N-point simulated data for each of the plurality of morphological features by generating N random samples from the gaussian KDE fitted to each of the plurality of sets of observational values;

construct a plurality of synthetic time domain signals for the time domain signal of interest from the N-point simulated data for each of the plurality of morphological features in accordance to the template, wherein the constructing of the plurality of synthetic time domain signals comprising:

determining a plurality of sequences derived from the generated N-point simulated data for each of the plurality of morphological features, wherein a plurality of elements in each of the plurality of sequences comprising Ts, Ps, Ds, Ns, $r_1$ $r_2$, $r_3$, $q_1$, $q_2$ and $q_3$, wherein values of $q_1$, $q_2$, $q_3$, $r_1$, $r_2$, $r_3$ are derived based on a preselected values of the distances $d_1$, $d_2$, $d_3$ defined for the template, and wherein position of each of the plurality of elements within each of the plurality of sequences is based on a set of conditions defined by a predefined set of morphological features among the plurality of morphological features;

generating from the plurality of sequences, a plurality of time domain signals corresponding to the time domain signal of interest by performing a spline fitting on each of the plurality of sequences, wherein the spline fitting utilizes piecewise linear regression to obtain parameters of lines connecting two successive elements among the plurality of elements of the each of the plurality of sequences;

smoothening each of the plurality of time domain signals using a smoothening technique to generate a plurality of smoothened time domain signals; and applying a peak smoothening technique on each of the smoothened plurality of time domain signals to construct the plurality of synthetic time domain signals for the time domain signal of interest; and build a two-stage cascaded classifier for classifying input data corresponding to the time domain signal of interest into one of the class data and the non-class data by using a combination of the plurality of samples in the parent dataset and the plurality of synthetic time domain signals as a training data, and wherein the two stage cascaded classifier comprises:

a first classifier utilizing Matusita distance for likeness measurement and data explosion driven decision rule for classification, wherein a plurality of statistical features is extracted from the plurality of synthetic time domain signals to differentiate between the class data and the non-class data, using a rule based on the Matusita distance; and a second classifier utilizing a random forest technique for classification, wherein constructing the two stage cascaded classifier using the training data is used to correct bias, test real time data corresponding to the time domain signal of interest and classify the real time data into the final class data and the final non-class data.

6. The system as claimed in claim 5, wherein
the first classifier classifies the input data as the non-class data and the class data with ambiguity, wherein the non-class data at an output of the first classifier is identified as a final non-class data, and
the second classifier classifies the received class data with ambiguity into a final class data.

7. The system as claimed in claim 5, wherein the one or more hardware processors are configured to utilize the two stage cascaded classifier to validate the plurality of synthetic time domain signals.

8. The system as claimed in claim 5, wherein the time domain signal of interest is a biosignal.

9. One or more non-transitory machine-readable information storage mediums comprising one or more instructions, which when executed by one or more hardware processors causes a method for:

receiving a parent dataset of a plurality of samples of a time domain signal of interest comprising a combination of a class data, wherein the class data refer to a subject with Coronary artery disease, CAD and a non-class data, wherein the non-class data refer to the subject without the CAD;

identifying a plurality of subsets, from the parent dataset, corresponding to a plurality of morphological features identified for the time domain signal of interest, wherein each subset among the plurality of subsets comprises p samples corresponding to the plurality of the morphological features, further wherein the plurality of morphological features comprise a Peak Sample (Ps), a Peak Amplitude (Pa), a Trough Sample (Ts), a Trough Amplitude (Ta), a Notch Sample (Ns), a Notch Amplitude (Na), a Dip Sample (Ds), a Dip Amplitude (Da), and distance between left and right samples corresponding to the 25%, 50%, 75% of the (Pa) defining distances $d_1$, $d_2$, $d_3$, and wherein the plurality of morphological features define a template for the time domain signal of interest;

processing each of the plurality of subsets corresponding to each of the plurality of morphological features to generate a plurality of sets of observational values with each of the plurality of sets of observational values comprising p actual values corresponding to each of the plurality of morphological features;

fitting a gaussian kernel density estimate (KDE) to each of the plurality of sets of observational values;

generating N-point simulated data for each of the plurality of morphological features by generating N random samples from the gaussian KDE fitted to each of the plurality of sets of observational values; and constructing a plurality of synthetic time domain signals for the time domain signal of interest from the N-point simulated data for each of the plurality of morphological features in accordance to the template, wherein the constructing of the plurality of synthetic time domain signals comprising:

determining a plurality of sequences derived from the generated N-point simulated data for each of the plurality of morphological features, wherein a plurality of elements in each of the plurality of sequences comprising Ts, Ps, Ds, Ns, $r_1$ $r_2$, $r_3$, $q_1$, $q_2$ and $q_3$, wherein values of $q_1$, $q_2$, $q_3$, $r_1$, $r_2$, $r_3$ are derived based on a preselected values of the distances $d_1$, $d_2$, $d_3$ defined for the template, and wherein position of each of the plurality of elements within each of the plurality of sequences is based on a set of conditions defined by a predefined set of morphological features among the plurality of morphological features;

generating from the plurality of sequences, a plurality of time domain signals corresponding to the time domain signal of interest by performing a spline fitting on each of the plurality of sequences, wherein the spline fitting utilizes piecewise linear regression to obtain parameters of lines connecting two successive elements among the plurality of elements of the each of the plurality of sequences;

smoothening each of the plurality of time domain signals using a smoothening technique to generate a plurality of smoothened time domain signals; and applying a peak smoothening technique on each of the smoothened plurality of time domain signals to construct the plurality of synthetic time domain signals for the time domain signal of interest; and building a two stage cascaded classifier for classifying input data corresponding to the time domain signal of interest into one of the class data and the non-class data by using a combination of the plurality of samples in the parent dataset and the plurality of synthetic time domain signals as a training data, and wherein the two stage cascaded classifier comprises:

a first classifier utilizing Matusita distance for likeness measurement and data explosion driven decision rule for classification, wherein a plurality of statistical features is extracted from the plurality of synthetic time domain signals to differentiate between the class data and the non-class data, using a rule based on the Matusita distance; and a second classifier utilizing a random forest technique for classification, wherein constructing the two stage cascaded classifier using the training data is used to correct bias, test real time data corresponding to the time domain signal of interest and classify the real time data into the final class data and the final non-class data.

* * * * *